United States Patent [19]

Dory

[11] Patent Number: 5,143,073
[45] Date of Patent: Sep. 1, 1992

[54] WAVE APPARATUS SYSTEM

[75] Inventor: Jacques Dory, Coupvray-Esblay, France

[73] Assignee: EDAP International, S.A., France

[21] Appl. No.: 206,385

[22] Filed: Jun. 14, 1988

Related U.S. Application Data

[60] Division of Ser. No. 37,369, Apr. 13, 1987, abandoned, which is a division of Ser. No. 728,905, Apr. 30, 1985, Pat. No. 4,658,828, which is a continuation-in-part of Ser. No. 674,889, Nov. 26, 1984, Pat. No. 4,617,931.

[30] Foreign Application Priority Data

Dec. 14, 1983 [FR] France .............................. 83 20041
May 3, 1984 [FR] France .............................. 84 06877

[51] Int. Cl.$^5$ ......................... A61B 8/00; A61N 5/00
[52] U.S. Cl. ......................... 128/660.03; 128/24 AA; 128/399
[58] Field of Search ............. 128/328, 660.03, 662.03, 128/399, 24 AA, 24 EL, 804

[56] References Cited

U.S. PATENT DOCUMENTS

| | | |
|---|---|---|
| 3,338,235 | 8/1967 | Gordon . |
| 3,735,755 | 5/1973 | Eggleton et al. . |
| 3,756,071 | 9/1973 | Dory . |
| 3,785,382 | 1/1974 | Schmidt-Kloiber . |
| 3,942,531 | 3/1976 | Hoff et al. . |
| 3,974,682 | 8/1976 | Soldner et al. . |
| 4,005,258 | 1/1977 | Dory . |
| 4,046,149 | 9/1977 | Komiya . |
| 4,058,114 | 11/1977 | Soldner . |
| 4,070,905 | 1/1978 | Kossoff . |
| 4,163,394 | 8/1979 | Soldner . |
| 4,218,768 | 8/1980 | Hassler . |
| 4,235,111 | 11/1980 | Hassler . |

(List continued on next page.)

FOREIGN PATENT DOCUMENTS

| | | |
|---|---|---|
| 0036353 | 9/1981 | European Pat. Off. . |
| 0045265 | 2/1982 | European Pat. Off. . |
| 0090138 | 10/1983 | European Pat. Off. . |
| 0108190 | 5/1984 | European Pat. Off. . |
| 0124686 | 11/1984 | European Pat. Off. . |
| 0133946 | 3/1985 | European Pat. Off. . |
| 654673 | 12/1937 | Fed. Rep. of Germany . |
| 2053892 | 5/1972 | Fed. Rep. of Germany . |
| 2223319 | 12/1972 | Fed. Rep. of Germany . |
| 2202989 | 7/1973 | Fed. Rep. of Germany . |
| 2351247 | 4/1975 | Fed. Rep. of Germany . |

(List continued on next page.)

OTHER PUBLICATIONS

Coleman et al., "Applications of Therapeutic Ultrasound in Opthalmology", reprinted from Progress in Medical Ultrasound, vol. Feb. 1981, Amsterdam, Excerpta Medica, pp. 263-270.
Ultrasonic Focusing Radiators, pp. 225-285, 306-307.
Berlinicke et al., "Uber Beeineflussung Von Gallensteinen Durch Ultraschall in Vitro", Klinistche Wochenschrift, Dec. 28, 1950, p. 390.
Mulvaney, "Attempted Disintegration of Calculi by Ultrasonic Vibrations", The Journal of Urology, vol. 70, No. 5, Nov. 1953, pp. 704-707.
Coats, "Application of Ultrasonic Energy to Urinary and Biliary Calculi", The Journal of Urology, vol. 75, No. 5, May 1956, pp. 865-874.
Bergmann, "Der Ultraschall- und Siene Anwendung in Wissen Schaft und Technik", S. Hirzel Verlag, Stuttgart, 1954, pp. 126-137.
Friedland, "Present Status of Ultrasound in Medicine", The Journal of the American Medical Association, vol. 163, No. 10, Mar. 1957, pp. 799-803.

Primary Examiner—Lee S. Cohen
Attorney, Agent, or Firm—William A. Drucker

[57] ABSTRACT

The disclosure relates to a device for locating and disintegrating body anomalies and displaying real time images of a body anomaly during treatment. The images are formed between pulses of disintegrating treatment waves by an ultrasound scanner in line with a shock wave treatment beam.

40 Claims, 2 Drawing Sheets

U.S. PATENT DOCUMENTS

| | | |
|---|---|---|
| 4,245,511 | 1/1981 | Soldner . |
| 4,274,421 | 6/1981 | Dory . |
| 4,281,661 | 8/1981 | Dory . |
| 4,287,770 | 9/1981 | Weyns . |
| 4,294,119 | 10/1981 | Soldner . |
| 4,311,147 | 1/1982 | Hausler . |
| 4,340,944 | 7/1982 | Dory . |
| 4,368,410 | 1/1983 | Hance et al. . |
| 4,373,395 | 2/1983 | Borburgh et al. . |
| 4,412,316 | 10/1983 | Diepers . |
| 4,434,341 | 2/1984 | Busby . |
| 4,458,533 | 7/1984 | Borburgh . |
| 4,462,092 | 7/1984 | Kawabuchi et al. . |
| 4,474,180 | 10/1984 | Angulo . |
| 4,478,083 | 10/1984 | Hassler et al. . |
| 4,484,569 | 11/1984 | Driller et al. . |

(List continued on next page.)

FOREIGN PATENT DOCUMENTS

| | | |
|---|---|---|
| 2645738 | 4/1977 | Fed. Rep. of Germany . |
| 2722252 | 11/1978 | Fed. Rep. of Germany . |
| 2913251 | 10/1980 | Fed. Rep. of Germany . |
| 2921444 | 11/1980 | Fed. Rep. of Germany . |
| 3119295 | 12/1982 | Fed. Rep. of Germany . |
| 3122056 | 12/1982 | Fed. Rep. of Germany . |
| 3142639 | 5/1983 | Fed. Rep. of Germany . |
| 3150513 | 6/1983 | Fed. Rep. of Germany . |
| 3210919 | 10/1983 | Fed. Rep. of Germany . |
| 3241026 | 5/1984 | Fed. Rep. of Germany . |
| 3316837 | 11/1984 | Fed. Rep. of Germany . |
| 3319871 | 12/1984 | Fed. Rep. of Germany . |

(List continued on next page.)

OTHER PUBLICATIONS

Fry, "Precision High Intensity Focusing Ultrasonic Machines for Surgery", American Journal of Physical Medicine, vol. 37, No. 3, Jun. 1958, pp. 152–156.

Fry et al., "Ultrasonic Visualization of Soft Tissue Structure Based on Gradients in Absorption Characteristics", The Journal of the Acoustical Society of America, vol. 35, No. 11, Nov. 1963, pp. 1788–1790.

Guilgkett; "Stobspannungen und Stobstrome" (source unkown), pp. 2–22.

Gekhman et al., "The Effect of Supersonic Waves upon the Kidneys and the Urinary Tract", (Russian) 1963, pp. 17–21.

Tarnoczy, "Sound Focussing Lenses and Wave Guides", Ultrasonics, Jul.–Sep., 1965, pp. 115–127.

Lele, "Production of Deep Focal Lesions by Focused Ultrasound–Current Status", Ultrasonics, Apr. 1967, pp. 105–112.

Kurtze, "Uber die Bedingunguen fur das Auftreten von Kavitation in Flussig Keiten", (source unknown), pp. 1–47.

Rozenberg, "Sources of High Intensity Ultrasound", Plenum Press, New York, 1969, vol. 1, Chapter 4, pp. 288–307.

Fry, "Ultrasonic Visualization", Confinia Neurologica, vol. 32, pp. 38–52, 1970.

Howards et al., "Current Status of Mechanical Lithotripsy", Transactions of the American Association of Genito–Urinary Surgeons, vol. 65, 1973, pp. 123–125.

Gavriiov et al., "Use of Focused Ultrasound to Accelerate the Maturing of a Cataract", Sov. Phys. Acoust., vol. 20, No. 3, Nov.–Dec. 1974, pp. 229–231.

Hausler, "Physikalische Grundlagen der Instrumentellen und der Extrakorporalen Zerkleinerung Von Harnsteinen" (source unknown), p. 32.

Hausler et al., "Ultraschallverfahren zur Ortung Von Nierensteinen" (source unknown), pp. 54–60.

Bittner, "Uber die Moglichkeiten, Nierensteine mit Hilfe des Ultraschall–A–Verfahrens Nachzuweisen und zu Lokalisieren" (source unknown), pp. 61–69.

Bartels, "Zur Frage der Nierenstein–Darstellung mit der B–Scan Sonographie" (source unknown), pp. 70–73.

Bartels, "Intraoperative Rontegenuntersuchungen der Niere mit dem Renodorgerat" (source unknown), pp. 74–81.

Wells, "Biomedical Ultrasonics", Academic Press, London, 1977, pp. 494–495.

Ibid., pp. 208–213.

Ibid., pp. 511–594.

Coleman et al., "Therapeutic Ultrasound in the Production of Ocular Lesions", American Journal of Opthalmology, 86:185–192, 1978.

Fry, "Ultrasound: Its Applications in Medicine and Biology", Elsevier Scientific Publishing Company, Amsterdam, 1978, pp. 689–745.

Hausler et al., "Properties and Physiological Application of Focussed Fluid Shock Waves", ASA Meeting, Honolulu, Hawaii, Dec. 1978, pp. 2–12.

Petersen, "Piezoelektrische Aktuatoren", Feinwerktechnik E. Messtechnik, 86 (1978), pp. 304–308.

Raudsz, "Pschrometrische Bestimmung", Feinwerktechnik & Messtechnik 86 (1978), p. 303.

Konrad et al., "Fokussierte Stobwellen zur Beruhrungsfreien Nierensteinzertrummerung an der Freigelegten Niere", Urologe A 18 (1979), pp. 289–293.

"Echographie Ultrasonore: Un Circuit CCD pour Simplifer l'Electronique de Commande", Mesures Regulation Auromatisme–Fevrier 1980, pp. 25–27.

(List continued on next page.)

U.S. PATENT DOCUMENTS

| | | |
|---|---|---|
| 4,486,680 | 12/1984 | Bonnet et al. |
| 4,536,673 | 8/1985 | Forster |
| 4,545,385 | 10/1985 | Pirschel |
| 4,564,980 | 1/1986 | Diepers |
| 4,586,512 | 5/1986 | Do-huu et al. |
| 4,617,931 | 10/1986 | Dory ............................ 128/328 |
| 4,618,796 | 10/1986 | Riedlinger |
| 4,618,887 | 10/1986 | Birk |
| 4,620,545 | 11/1986 | Shene et al. |
| 4,639,904 | 1/1987 | Riedlinger |
| 4,658,828 | 4/1987 | Dory ......................... 128/660.03 |
| 4,671,292 | 6/1987 | Matzak |
| 4,721,106 | 1/1988 | Kurtze et al. |

FOREIGN PATENT DOCUMENTS

| | | |
|---|---|---|
| 3328068 | 2/1985 | Fed. Rep. of Germany |
| 3426398 | 3/1986 | Fed. Rep. of Germany |
| 2247195 | 5/1975 | France |
| 2477723 | 9/1981 | France |
| 2487664 | 2/1982 | France |
| 2487665 | 2/1982 | France |
| 2546737 | 12/1984 | France |
| 3589715 | 5/1987 | France |
| 8400504 | 9/1985 | Netherlands |
| 2113099 | 8/1983 | United Kingdom |
| 2140693 | 12/1984 | United Kingdom |
| 602180 | 4/1978 | U.S.S.R. |

OTHER PUBLICATIONS

Chaussy, "Beruhrungsfreie Nierensteinzertrummerung Durch Extrakorporal Erzeugte, Fokussierte Stobwellen", Beitrage zur Urologic, vol. 2, Karger, Basel, 1980, pp. 40–41, Translation of entire source included, Chaussy et al., Extracorporeal Shock Wave Lithotripsy-New Aspects in the Treatment of Kidney Stone Disease, Karger, Basel, 1982.

Coleman et al., "Ultrasonically Accelerated Resorption of Vitreous Membranes", American Journal of Opthalmology, 89:490–499, 1980.

Lizzy et al., "Experimental Treatment of Intra-ocular Carcinoma with High Intensity Focused Ultrasound", Paper No. 1305, Proceedings of the 25th Annual Meeting of the American Institute of Ultrasound in Medicine, Sep. 15–19, 1980, New Orleans, Lousiana.

Hausler and Stein, "Fokussierbare Unterwasserimpulsschallquellen", Acustica, vol. 49, No. 4, 1981, pp. 273–279.

Coleman et al., "Production of Alternate Filtration Paths for Treatment of Glaucoma with High Intensity Ultrasound", Paper No. 1303, AIUM/SDMS Annual Convention, San Francisco, California, Aug. 17–21, 1981.

Bulow et al., "Electrohydraulic Lithotripsy with Aspiration of the Fragments Under Vision-304 Consecutive Cases", The Journal of Urology, vol. 126, Oct. 1981, pp. 454–456.

Riedlinger et al., "Generation of High Energy Ultrasound Impulses with Focusing Piezoelectric Transducers", Fortschritte der Akustik, FASA/DAGA '82, Gottingen, 1982, pp. 755–758.

Chaussy et al., "First Clinical Experience with Extracorporeally Induced Destruction of Kidney Stones by Shock Waves", The Journal of Urology, vol. 127, Mar. 1982, pp. 417–420.

Ziegler et al., "Erfahrungen mit Hochenergetischen Stobwellen Bei der Behandlung Von Nierensteinen", Results of High Intensity Shock Wave Treatment of Renal Calculi, Piezoelectric Ceramics, Ghent, Belgium, 1982.

Program of the 7th Annual Meeting, European Intrarenal Surgery Club, Ghent, Belgium, 1982.

Watanabe et al., "Micro-Explosion Cystolithotripsy", The Journal of Urology, vol. 129, Jan. 1983, pp. 23–28.

Hunt et al., "Ultrasound Transducers for Pulse-Echo Medical Imaging", IEEE Transactions on Biomedical Engineering, vol. BME-30, No. 8, Aug. 1983, pp. 453–481.

Chaussy et al., "Extracorporeal Shock Wave Lithotripsy (ESWL) for Treatment of Urolithiasis", Special Issue to Urology, vol. 23, No. 5, May 1984, pp. 59–66.

Elder et al., "Ultrasonic Lithotripsy of a Large Staghorn Calculus", The Journal of Urology, vol. 131, Jun. 1984, pp. 1152–1154.

Hynynen et al., "A Clinical Hyperthermia Unit Utilizing an Array of Seven Focused Ultrasonic Transducers", 1983 Ultrasonics Symposium, IEEE, pp. 816–821.

Chaussy et al., "Extrakorporale Stobwellenlithotripsie-Beginn einer Umstrukturierung in der Behandlung des Harnsteinleidens", Urologe A, vol. 23, 1984, pp. 25–29.

Chaussy et al., "Shock Wave Treatment for Stones in the Upper Urinary Tract", Urologic Clinics of North America, vol. 10, No. 4, Nov. 1983, pp. 743–750.

Brannen et al., "Ultrasonic Destruction of Kidney Stones", Original Clinical Articles, Mason, Clinic, Seattle, Feb., 1984, vol. 140, No. 2, pp. 227–232.

Lizzy et al., "Thermal Model for Ultrasonic Treatment of Glaucoma", Ultrasound in Med. & Biol., vol. 10, No. 3, 1984, pp. 289–298.

Wanner et al., "Problematik Einer Integrierten Ultraschallortung Im Versuchsmodell Beruhrungsfreie Nierensteinzertrummerung", Symposium Biophysikalische Verfahren Zur Diagnose und Therapie Von Steinleiden der Harnwege, Meersburg, Jul. 10 and 11, 1976, pp. 235–240.

WAVE APPARATUS SYSTEM

CROSS REFERENCE TO PRIOR APPLICATIONS

This is a division of Ser. No. 037,369, filed Apr. 13, 1987, abandoned, which is a division of Ser. No. 728,905, filed Apr. 30, 1985, which is U.S. Pat. No. 4,658,828, now U.S. Pat. No. Re. 33,590 of May 21, 1991 which is a continuation-in-part of Ser. No. 674,889, filed Nov. 26, 1984, now U.S. Pat. No. 4,617,831, now Re-Examination Certificate B1-4,617,931 of Jul. 12, 1988.

BACKGROUND OF THE INVENTION

The invention proposes applying ultrasound waves to surgical examination and treatment of anatomic anomaly targets within a body through the skin; and provides a system of apparatus which combines the three functions of localizing a target structure in the zone to be treated; of treating with elastic shock waves in a well controlled way in a well defined restricted region within this zone; and simultaneously checking the progressive results of the treatment with ultrasound during treatment.

SUMMARY OF THE INVENTION

The invention combines a generator exciting a pulsed focused elastic shock wave treatment beam comprising a main wave emitter and a main transducer, with a separate echography in-line ultrasound imaging device comprising an auxiliary high frequency pulse generator associated with an auxiliary piezoelectric transducer and with means causing the zone to be treated to be swept, during treatment, by the ultrasound examination beam generated by the auxiliary transducer.

The invention advantageously comprises a first auxiliary ultrasound locating operation mode during which emission of the examination beam as scanning pulses by at least one auxiliary transducer is effected; and preferably a second auxiliary mode for checking the focal region, during which reduced power periodic emission of the treatment beam is effected. Echos are received by the scanner. The main emitter is synchronized by the synchronization circuit of the auxiliary generator for echographic operation.

During the auxiliary operating modes for obtaining accurate adjustments, the quality of the echographic image, either of the anomaly in the zone located within a body to be treated (locating mode) or of the focal region (mode for checking the restricted region), will be substantially better than during the treatment mode, during which successive images of the zone to be treated will follow each other for example at intervals of the order of up to a second, which however allows the position of the focal region to be checked satisfactorily during treatment.

The invention includes switching and adjusting means causing, during main power treatment and checking operations, the pulsed emission of a treatment sequence of vibration elastic shock wave discharges as a focused beam by the main transducer, energized by the main emitter, during periodic time intervals separated by time intervals during which formation of echographic images is carried out.

In a preferred embodiment, the auxiliary transducer is linked in line to the treatment device which may comprise a curved concave focusing surface and thus, during movement of the focusing device to aim the treatment beam and to bring the treatment focal spot into successive restricted regions of the zone, the auxiliary transducer will at all times, except when the treatment beam operates, supply a real time image of a target structure in the treated region and of the zone which surrounds it, thus allowing a continuous check of the treatment zone to be effected easily and accurately.

BRIEF DESCRIPTION OF THE DRAWINGS

Other features and advantages of the invention will be clear from the following description.

In the accompanying drawings.

DESCRIPTION OF THE PREFERRED EMBODIMENT

Figure 2:
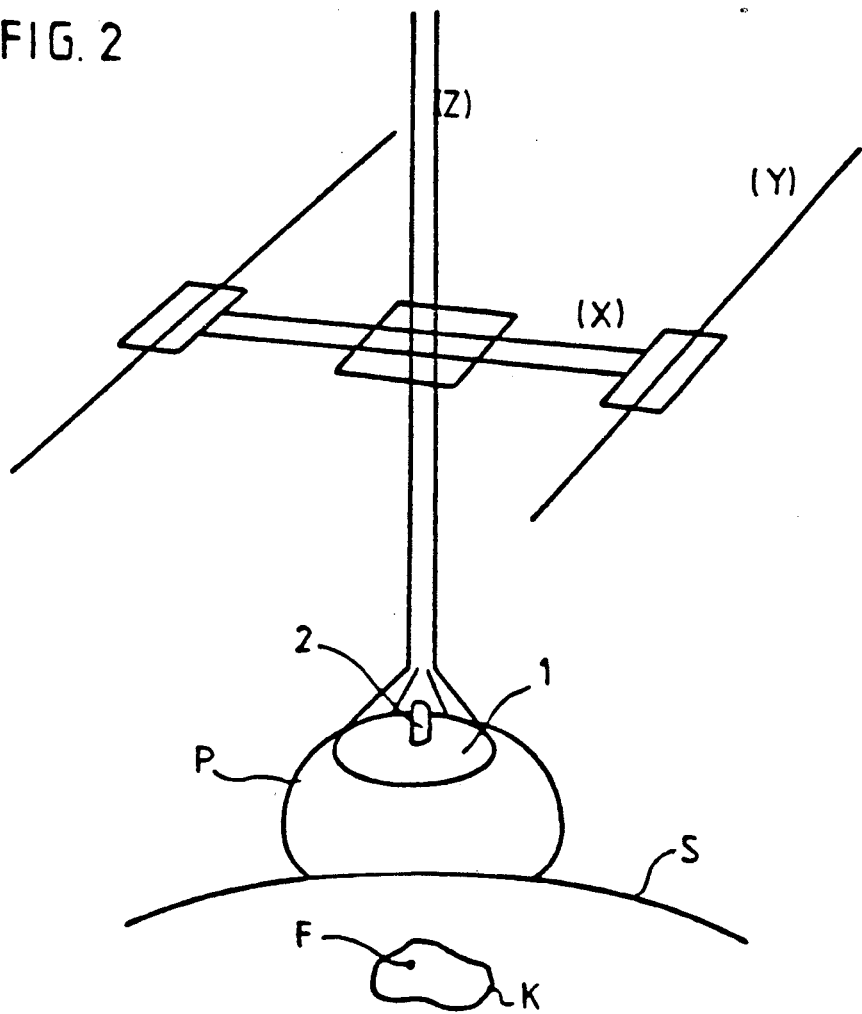
FIG. 2 shows schematically in perspective the main transducer and its adjustable support device.

In FIG. 2 is shown a main transducer 1 in the form of a spherical segment concave focusing surface supported by a mount which allows it to adjust position and to move in any order along three orthogonal axes X, Y and Z. This mount has been shown schematically, its construction being within the scope of a man skilled in the art. The focal spot formed in the center F of the sphere may, with this technique, be very small (diameter of 2 or 3 mm for example) and have a position which is strictly fixed for a given position of the transducer.

Generally in line along or in the direction of an axis of the spherical segment in the direction of the shock wave transmission path to the target there is disposed at least one auxiliary transducer 2 of a generally cylindrical shape which preferably passes through segment 1 and is fixed thereto. The ultrasound scanning device is preferably coaxial with the treatment focusing means and lies in line along the shock wave path to the target.

A pocket of water P is placed between the segment 1 and a patient so that the water or the pocket wall may contact the skin surface S of the body of the patient, who is assumed to be lying flat on a horizontal plane to provide an acoustic skin coupling through a portion of the body.

Figure 1:
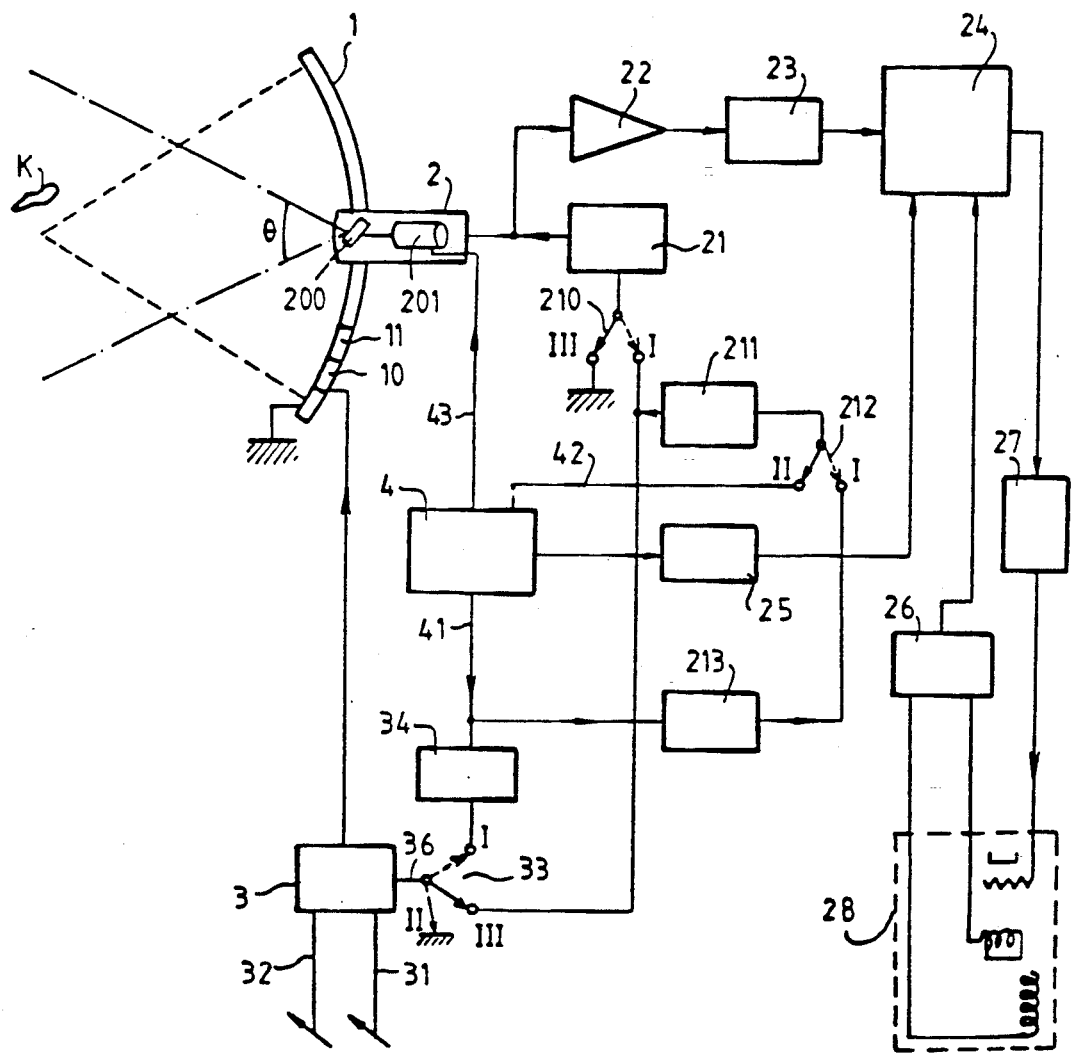
FIG. 1 is a general diagram of apparatus according to a preferred embodiment of the invention.

The concave curved focusing segment 1 has for example a diameter of 200 to 300 mm and when it is an active surface is formed from a large number (300 or 400) of piezoelectric elements 10, 11, etc . . . (FIG. 1) isolated from each other and juxtaposed to form a mosaic. The elements are metallized on both faces, one of the metallizations being connected to ground and the other to connections for energization by a main emitter 3 (FIG. 1).

Preferably, the elements of treatment transducer 1 are divided into groups or arrays each energized by a separate emitter (rectangle 3 symbolizing the assembly of these emitters), the elements of each group being spaced apart in the same circular zone of the spherical surface. By adjusting the relative phases of emissions, it is possible to modify the energy distribution in the focusing region of the ultrasound beam.

Emitter 3 delivers an electric signal to form interrupted periodic high frequency shock waves (500 KHz for example) during treatment as elastic ultrasound vibration shock wave discharges separated by interruption time intervals for the echography device to form an image. Operating conditions may be provided by emitters using power transistors.

An input 31 to emitter 3 symbolizes means for adjustment of the emitted power and an input 32 symbolizes means for adjustment of the pulse shape or wave duration.

In FIG. 1 it can be seen that the ultrasound scanning auxiliary transducer 2, which may comprise an active surface, is itself connected both, to a separate high frequency electric pulse emitter 21 and to a reception amplifier 22 followed by an analog-digital converter 23, itself followed by a memory 24. Emitter 21 can be connected to and synchronized by a pulse generator 211 which delivers for example a sequence of 256 pulses during successive time intervals of 1/10 second. Each of these time intervals corresponds to a complete sweep of a given angular sector (FIG. 1) by the beam emitted by transducer 2.

Transducer 2 is advantageously of the type described in U.S. Pat. No. 4,418,698, granted Dec. 31, 1983, comprising an oscillating piezoelectric element 200 controlled by a motor 201, itself controlled by an electronic circuit which is shown symbolically by a rectangle 4. This circuit provides control signals for the motor 201 housed inside the case of the transducer 2 and is adapted so that a complete oscillation of the motor corresponds to the above defined duration for forming an image (1/10 second).

In a first operation mode (treatment and checking) switch 210 is in position 1 as well as switches 212 and 33. In position 1 of switches 33 and 212, generator 211 is synchronized by a first output 41 of circuit 4, which is adjusted by means, not shown, for generating signals at its output 43 connected to motor 201. A scan is then swept, through the body, and the echos are converted to displayed electric signals. This is followed by a time interval during which no image is formed.

During intervals between the sweep periods, a circuit 34 generates square waves which synchronize emitter 3, whereas during sweep periods, a circuit 213 generates square waves of 1/10 second which synchronize the generator 211.

Thus, in this operating mode, transducer 1 generates an interrupted shock wave beam whereas the echography device forms an image for example every second in the intervals or interruptions between the treatment waves.

In a second operating mode (locating) with switch 210 in position 1, switch 33 is in position 11, so that emitter 3 is not synchronized and the focused treatment beam is not emitted. Switch 212 is also in position 11 so that generator 211 is synchronized by a second output 42 of circuit 4 which is adjusted to generate signals at its output 43. The echograph sweeps are separated by intervals and images are formed from echos converted to electric signals coming from reflection of the pulses generated by transducer 2. Generator 211 delivers the signals.

In a third operating mode (checking the focal region), switch 210 is in position 111, so that the emitter 21 and transducer 2 do not emit. Switch 212 is again in position 11 so that generator 211 is synchronized by the output 42 of circuit 4 which is adjusted, as in the second operating mode. Switch 33 is in position 111 and consequently emitter 3 is synchronized by the generator 211 which then delivers the signals In this third operating mode, the echographic device is therefore formed by emitter 3, transducer 1 operating for emission and transducer 2 operating for reception. The result is that an image is obtained of the distribution of the concentration of energy in the focal region emitted by the transducer 1.

Echographic signals reflected from surfaces in the treated zone received at 22 in the first or third operating modes are, after analog-digital conversion at 23, stored line by line in memory 24, a writing addressing device 25, controlled by circuit 4, causing the respective deflection angles of the beam emitted and/or received by transducer 2 to correspond with the respective lines of the memory. A device 26 for rapid reading of the memory energizes the X and Y deflection coils of a cathode ray tube 28, so the brightness control electrode receives the corresponding contents from memory 24, transformed into an analog-signal by a digital-analog converter 27. The electrical signals from the echos are then displayed as an image of the anomaly in the zone.

Practical construction of all the circuits described and shown is within the scope of a man skilled in the art.

Figure 3:
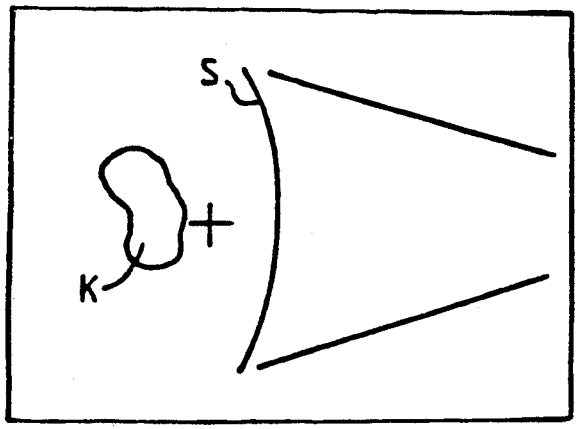
FIG. 3 illustrates the image obtained on the display screen which the apparatus comprises.

The apparatus which has been described operates as follows:

In the locating operating mode, the operator searches for and localizes the anomaly in the zone to be treated and/or altered. The display device is adapted, in a way known per se, to materialize a cursor mark on the screen of the cathode ray tube (for example by a cross) indicating the theoretical position of the focal spot of the treatment beam in the sectional plane shown, which plane passes through the axis of symmetry of transducer 1. The mark and zone are then brought into and maintained in coincidence to aim the treatment beam. The treatment transducer 1 is connected to the examination scanner 2. (It is a matter of B type echography). The operator begins aiming by moving transducer 1, in any order, for example, along axis X, until the treatment zone appears clearly on the screen, then he moves it for example along axes Y and Z, until the cursor cross mark coincides with the central region of the image in the zone of the anatomical anomaly (K, FIG. 3).

At this stage, the switches may be placed in position for checking the focal region: this region is then visible on the screen with a luminosity proportional to the corresponding distribution of energy concentration. Thus a representation is obtained of what the distribution of energy of the treatment wave will be during treatment which allows adjustments to be checked and perfected.

During treatment, the apparatus supplies, for example, only one image per second, but this rate is sufficient for substantially continuously checking the position of the focal spot.

It is clear that the apparatus described allows the evolution of the treatment to be checked during and after each treatment sequence. It is evident that different modifications may be made thereto, even according to other embodiments, without departing from the scope and spirit of the invention.

I claim:

1. Wave apparatus for treating a target within a body of transmitting energy across the skin comprising:
    (a) a treatment transducer generating a wave treatment beam focused within the body on a target and drive means exciting said treatment transducer;
    (b) means displacing said treatment transducer to aim said beam and to treat said target with said treatment beam;

(c) at least one separate imaging transducer generating a scanning ultrasound beam; said imaging transducer coupled to said treatment transducer; and (d) at least one echography device comprising said imaging transducer, means effecting real time scanning of said target with said scanning beam, receiver means coupled to said imaging transducer receiving echoes formed by reflection of said scanning beam on reflecting surfaces of said target; and image forming means coupled to said receiver means converting said echoes into displayed images of said target; said image forming means further displaying a mark which indicates the position of a focus of said treatment beam; and treatment beam aiming means to bring said mark and said images into coincidence.

2. Apparatus as claimed in claim 1 wherein said means for effecting scanning by said scanning ultrasound beam provides a sweep of said scanning beam in a plane which passes through an axis of symmetry of said treatment transducer.

3. The apparatus of claim 1 wherein said apparatus includes heating means for effecting hyperthermia.

4. The apparatus of claim 1 wherein said wave treatment beam is an ultrasonic beam.

5. Apparatus for treating a target within a body comprising:

(a) transducer means generating a wave treatment beam focused along a path including said target at a focus and drive means exciting the transducer means;

(b) separate real time imaging transducer means generating a scanning ultrasound examination beam; and (c) means effecting scanning of said target with said scanning beam within said path, said imaging transducer means receiving echoes reflecting from surfaces within said target;

(d) image forming and display means coupled to said imaging transducer means displaying real time images of said target;

(e) further means displaying a mark which indicates the position of said focus; and (f) treatment wave aiming means bringing said mark and said images into coincidence.

6. The apparatus of claim 5 wherein said apparatus includes heating means for effecting hyperthermia.

7. The apparatus of claim 5 wherein said wave treatment beam is an ultrasonic beam.

8. Apparatus for treating an internal body zone with waves comprising:

(a) treatment transducer means generating a wave treatment beam and focusing means focusing said wave treatment beam in said zone at a focus along a treatment path and drive means exciting said treatment transducer means;

(b) separate imaging transducer means generating a scanning examination ultrasound beam scanning across said treatment beam path, said imaging transducer means being located in line with said treatment path and connected with said treatment transducer means; and (c) means effecting scanning of said zone with said scanning beam, said imaging transducer means receiving echoes reflected from surfaces within said zone; and (d) image forming and display means coupled to said imaging transducer means and displaying real time images of said zone;

(e) means further displaying a mark which indicates the position of said focus of said treatment beam; and (f) means bringing said mark and said images into coincidence.

9. The apparatus of claim 8 wherein said apparatus includes heating means for effecting hyperthermia.

10. The apparatus of claim 8 wherein said wave treatment beam is an ultrasonic beam.

11. A device for focused wave treatment of a target in a body, said device comprising:

(a) wave generator means driving transducer means;

(b) treatment transducer means responsive to said generator means for generating a treatment wave beam;

(c) means focusing said treatment wave beam at a focal spot;

(d) means connecting said generator means to said transducer means;

(e) echographic beam transmitter-receiver means for transmitting and receiving an echographic beam;

(f) image forming and display means coupled to said transmitter-receiver means displaying real time serial two dimensional images of said target; means displaying a visual indication of the position of said focal spot and scanning means effecting successive sweeps of said echographic beam; and (g) means displacing and aiming said means focusing said treatment wave beam means to bring said images and said indication into coincidence.

12. The device as claimed in claim 11, wherein:

(a) said scanning means effects sectorial sweeps of the echographic beam, said sectorial sweeps being effected in a plane which passes through an axis of said means for focusing; and (b) said transmitter-receiver means is coaxial with said treatment wave beam focusing means.

13. The device as claimed in claim 11 wherein said treatment transducer means includes a piezoelectric transducer.

14. The device as claimed in claim 11, wherein said means displacing said focusing means controls displacement of said treatment beam along orthogonal axes; and said means displaying said visual indication displays the position of said focal spot in a plane passing through an axis of said focusing means.

15. The device as claimed in claim 11, said device further comprising first means substantially reducing the power output of said wave generator means, while the latter is connected to said treatment transducer means; second means synchronizing the frequency of said wave generator means with the frequency of treatment transducer means, and switching means placing said first and second means into service to display an image of the energy distribution reflected from the region of the target when the treatment transducer means is operated at reduced power output.

16. The apparatus of claim 11 wherein said apparatus includes heating means for effecting hyperthermia.

17. The apparatus of claim 11 wherein said wave treatment beam is an ultrasonic beam.

18. A device for wave treatment of a target structure within a body comprising:

(a) means generating a treatment wave and means focusing said wave at a focal spot;

(b) image forming and display means displaying serial two dimensional images of said target structure and means displaying a visual indication of the position of said focal spot;

(c) said image forming and display means comprising echographic beam transmitter-receiver means for generating and receiving an echographic beam and scanning means coupled to said transmitter-receiver means, effecting successive sweeps of said echographic beam to form said images; and (d) treatment wave aiming means displacing said treatment wave generating means and said transmitter-receiver means to bring said images and said indication into coincidence.

19. The device of claim 18 in which the transmitter-receiver means is coaxial with said means generating a treatment wave.

20. The device of claim 18 in which the transmitter-receiver means is located between said treatment wave focusing means and said focal spot.

21. The apparatus of claim 18 wherein said apparatus includes heating means for effecting hyperthermia.

22. The apparatus of claim 18 wherein said treatment wave is an ultrasonic beam.

23. A device for spatial location and destruction of a target in a patient, comprising wave transducer means producing treatment waves, having an axis of symmetry and a focus alignable with the target to be destroyed, B-scanner means arranged to generate a B-section image of bodily tissue of said patient traversed by treatment waves from said transducer means, displaceable support means mounting said B-scanner means to move with said transducer means, monitor means displaying said image, means defining at least one mark on said monitor means indicating the position of the focus, and means effecting relative movement between said patient and a device to aim the treatment waves and to bring said target depicted in said image into coincidence with said mark, said wave transducer means being adapted to generate treatment waves to destroy said target at said focus.

24. A device according to claim 23 wherein the support means mounts the B-scanner means with the symmetry axis of the treatment wave transducer means and the support means in coincidence.

25. The device according to claim 23 wherein the treatment wave transducer means comprises individual piezoelectric transducer elements assembled into the form of a spherical cap, and wherein the displaceable support means extends through a part of the treatment wave transducer means which is unobstructed by transducer elements.

26. The apparatus of claim 23 wherein said apparatus includes heating means for effecting hyperthermia.

27. The apparatus of claim 23 wherein said treatment waves are in an ultrasonic beam.

28. A device for spatial location and destruction of a target in a patient, comprising focusing wave transducer means producing treatment waves and having an axis of symmetry and a focus alignable with the target to be destroyed, B-scanner means arranged to generate a B-section image of bodily tissue of the patient traversed by the treatment waves from said transducer means, displaceable support means mounting the B-scanner means to move with the transducer means, monitor means displaying said image, means defining at least one mark on said monitor means indicating the position of the focus, and means effecting relative movement between the patient and the device to bring the target depicted in said image into coincidence with said mark.

29. A device according to claim 28 wherein the support means mounts the B-scanner with the symmetry axis of the wave transducer means and the longitudinal axis of the B-scanner coinciding.

30. A device according to claim 28 wherein the wave transducer means comprises individual piezoelectric transducer elements assembled into the form of a spherical cap, and wherein the support means extends through a part of the wave transducer means which is unobstructed by transducer elements.

31. The apparatus of claim 28 wherein said apparatus includes heating means for effecting hyperthermia.

32. The apparatus of claim 28 wherein said treatment waves are in an ultrasonic beam.

33. Locating and positioning apparatus for a focusing treatment wave system for noninvasive treatment of a target within a body of a patient comprising:
patient support means establishing a position of a body of a patient,
an ultrasonic scanning device mounted on further support means to permit the device to assume different positions with respect to a patient body;
image display means providing a reference representation with respect to a geometric point outside said further support means, permitting through ultrasonic imaging coincidence of said point with said target;
a treatment wave system including a treatment wave generator and focusing device mounted on said further support means;
means connected to said further support means and movable therewith having a disposition in relation to a focal point of the treatment wave system for obtaining positional correlation of said representation with said focal point in an imaging plane defined by the ultrasonic scanning device to image the target internal to the body by the ultrasonic scanning device and then treat the target with the treatment wave system while the body remains positioned on the support means and the reference representation remains coincident with an image of the target during treatment.

34. The apparatus of claim 33 wherein said apparatus includes heating means for effecting hyperthermia.

35. The apparatus of claim 33 wherein said treatment wave system is an ultrasonic beam.

36. Locating and positioning apparatus for a focusing treatment wave device for noninvasive treatment of a target within a body of a patient comprising:
(a) a focusing treatment wave device having a focus;
(b) patient support means establishing a position of a body of a patient;
(c) an ultrasonic scanning device mounted to permit the device to assume with the treatment wave device different positions vis a vis a stationary patient body;
(d) image display means including a reference mark indicating the position of the focus of the treatment device and an image of the target; and
(e) means to move the mark into register with the target image to aim the treatment wave device at the target in a stationary patient.

37. Apparatus for ultrasonically treating a subject volume comprising:
(a) a first transducer having a transmitting surface and means for generating a first treatment beam focused in a restricted focal zone and drive means for exciting ultrasonic treatment vibrations within the first transducer;

(b) means for displacing the first transducer with respect to predetermined axes of coordinates to treat subject volume with said first treatment beam;

(c) a second transducer for generating an ultrasound examination beam, said second transducer having an active surface which is substantially smaller than that of the transmitting surface of the first transducer, said second transducer being connected with the first transducer during the displacement of the first transducer; and (d) an echography device comprising said second transducer, electric pulse generator means coupled to and driving said second transducer, means for effecting a scanning of an examination volume with said second transducer for receiving the echoes formed through reflection of said ultrasound examination beam on reflecting surfaces within the examination volume and image forming means coupled to means for displaying images of the examination volume, said focal zone being located in a predetermined relative position within the examination volume, said image forming means further displaying a mark which indicates said predetermined position of the focal zone and means to bring said mark and image into coincidence.

38. The apparatus of claim 37 wherein said apparatus includes heating means for effecting hyperthermia by means causing local heating from the first transducer and means adapted to focus the first transducer at a focal spot.

39. Apparatus for treating a subject volume comprising:

(a) a first transducer having a transmitting surface and means for focusing a first treatment beam in a restricted focal zone and drive means for exciting treatment vibrations within the first transducer;

(b) means for displacing the first transducer with respect to predetermined axes of coordinates to treat subject volume with said first treatment beam;

(c) a second transducer for generating an ultrasound examination beam, said second transducer having an active surface which is substantially smaller than that of the transmitting surface of the first transducer, said second transducer being connected with the first transducer during the displacement of the first transducer; and (d) an echography device comprising said second transducer, electric pulse generator means coupled to and driving said second transducer, means for effecting a scanning of an examination volume with said ultrasound examination beam, receiver means coupled to said second transducer for receiving the echoes formed through reflection of said ultrasound examination beam on reflecting surfaces within the examination volume and image forming means coupled to the receiver means for displaying images of the examination volume, and focal zone being located in a predetermined relative position within the examination volume, said image forming means further adjusting a mark which indicates said predetermined position of the focal zone and means to bring said mark and image into coincidence.

40. The apparatus of claim 39 wherein said treatment beam is an ultrasonic beam.

* * * * *